United States Patent [19]
Krygeris et al.

[11] 3,970,393
[45] July 20, 1976

[54] AUTOMATIC COMPENSATION FOR DENSITOMETER IMBALANCE

[75] Inventors: Algirdas J. Krygeris, Richmond Heights; John M. Manring, Cleveland Heights, both of Ohio

[73] Assignee: Harris Corporation, Cleveland, Ohio

[22] Filed: July 23, 1974

[21] Appl. No.: 490,981

[52] U.S. Cl. .............................. 356/195; 250/559; 356/206; 356/212
[51] Int. Cl.² ...................... G01J 3/46; G01N 21/48
[58] Field of Search ........... 356/211, 212, 179, 195, 356/205, 206, 229; 250/559

[56] References Cited
UNITED STATES PATENTS
3,748,046  7/1973  Murray ............................. 356/212
3,756,725  9/1973  Manring ........................... 356/211

*Primary Examiner*—Vincent P. McGraw

[57] ABSTRACT

A method for compensating measurements of optical density of ink printed by a printing press in which amounts of light reflected from a printed test patch area and from an adjacent unprinted reference area are measured. The measurement sensitivity of sensing apparatus for measuring light from the printed test area need not be equal to the measurement sensitivity of sensing apparatus for measuring light from the unprinted reference area because the relative sensitivities of the two sensing apparatuses are ascertained before the press starts printing. The relative sensitivities are ascertained by making preliminary measurements of light from areas known to have equal reflection densities, for example unprinted paper. The results of these preliminary measurements are stored in a memory and employed later automatically to compensate density measurements based on readings made by the two sensing apparatuses while the press is printing.

4 Claims, 5 Drawing Figures

AUTOMATIC COMPENSATION FOR DENSITOMETER IMBALANCE

BACKGROUND OF THE INVENTION

Various types of optical reflection densitometers have been used in the prior art to measure the optical density of ink printed on paper or other stock by printing presses. One type, illustrated by U.S. Pat. No. 3,748,046 to James E. Murray, measures light reflected from the paper and also measures reference light not reflected from the paper, for example reference light relected from a reference area built into the densitometer; the light measurements are combined to produce indications of ink density.

A second type of prior densitometer measures only light which is reflected from the paper. A densitometer of the second type is described in U.S. Pat. No. 3,756,725, to J. M. Manring, in which a densitometer head is placed close to a rotating cylinder of a printing press, and a flash lamp in the densitometer head illuminates both a printed test patch area and an adjacent unprinted reference area on paper on which images and test patches were printed by the press. In U.S. Pat. No. 3,756,725, the flash lamp was used in common for simultaneous measurement of the reflectivity of both the printed test patch area and the unprinted reference area, and separate sensing apparatuses were employed for measuring the reflected light from the printed and unprinted areas respectively. Measurements made by the two measurement apparatuses for areas of the same optical density can be made equal by occasional manual adjustment of a gain setting device in at least one of the two measurement apparatuses of U.S. Pat. No. 3,756,725. The gain adjustment device can be manually adjusted to produce a density reading of zero when equal reflectivity surfaces are measured simultaneously by the two measurement apparatuses. The resulting gain setting produces equal overall measurement sensitivity for the test patch and the reference area measurement apparatuses. Unprinted paper is ordinarily put into the press to make the gain adjustment.

The present invention relates to the second type of densitometer, and in particular to compensating its density readings automatically to account for differences in measurement sensitivities of its two measurement apparatuses without adjusting their gains to have equal sensitivities.

SUMMARY OF THE INVENTION

In accordance with the present invention the reflection density of ink printed by a printing press is measured by simultaneously measuring the reflection density of a printed test patch area and an unprinted reference area illuminated by the same light source. Separate sensing apparatuses of the densitometer are employed for measuring light reflected from the printed and unprinted areas respectively. It is not necessary, however, to adjust the relative measurement sensitivities of the two sensing apparatuses so as to be equal. Instead their relative measurement sensitivity is measured, in advance of operation of the press, by measuring equally reflective areas, (for example areas of unprinted paper), with both of the sensing apparatuses and storing the calibration data thus obtained in a memory. Subsequently, when the press is operating and light measurements are made from printed and unprinted reference areas, the stored data regarding relative overall measurement sensitivities of the two channels are read out from the memory and employed to compensate the currently made measurements to provide correct output data of reflection density of ink as printed by the press.

Other aspects and features of the invention are also described herein and are illustrated in the figures.

DESCRIPTION OF A PREFERRED EMBODIMENT

Figure 1:
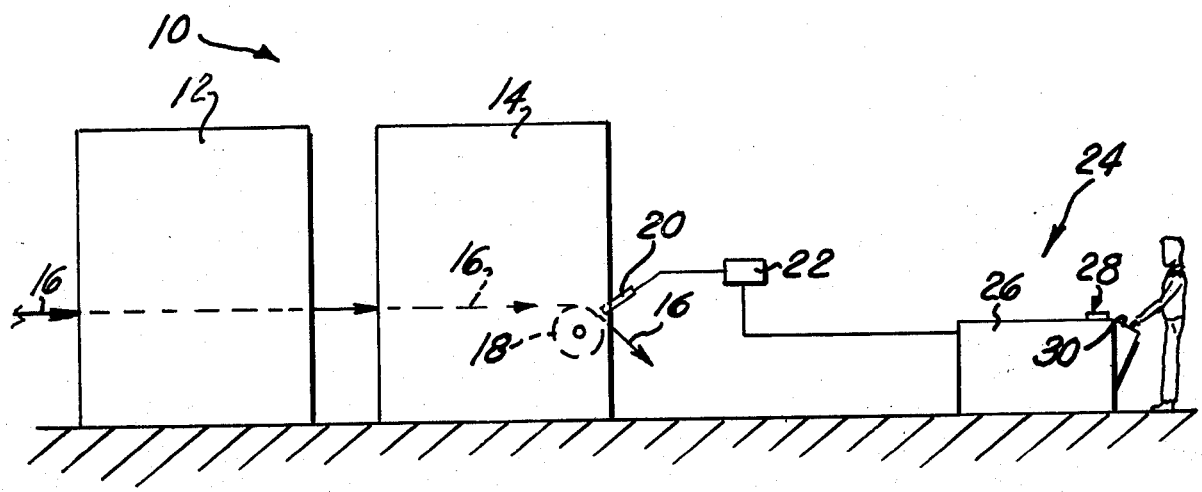
FIG. 1 is a side view of a printing press having two printing units and an optical densitometer.

In a preferred embodiment of the invention, a lithographic printing press 10 has two printing units 12, 14 each printing a different color of ink on paper or other stock 16 that travels through the two printing units in succession, FIG. 1. The printing units 12, 14 have rotating cylinders, and the completely printed paper 16 is in contact with a portion of the periphery of one of the rotating cylinders 18 near the output of the second printing unit 14. Supported near the cylinder 18 are several densitometer heads 20 for making measurements of optical reflection density of the printed paper 16 upon receiving an automatic command. An electronic unit 22 is associated with the densitometer head 20, and a cable of electrical conductors connects the electronic unit 22 with additional apparatus in an inspection and control station 24. The station 24 includes an inspection table 26 on which specimens of paper printed by the press can be spread out, control switches 28, and a display and control panel 30, which displays to the operator the results of density data gathered by the densitometer head 20, and other data.

Figure 2:
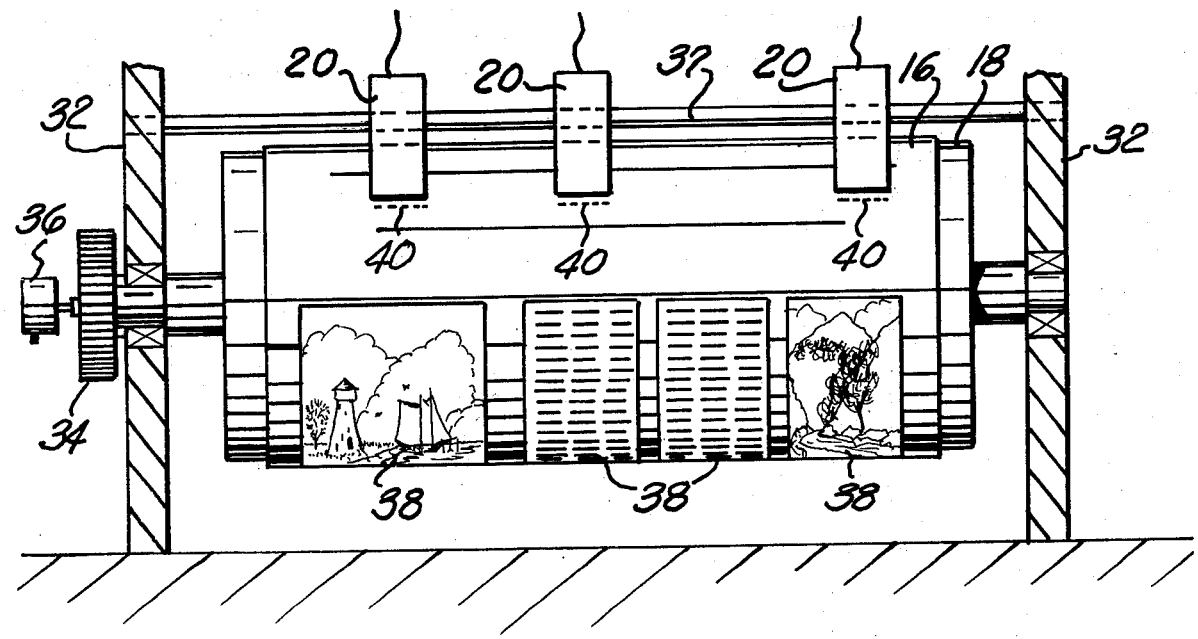
FIG. 2 shows a cylinder of a printing press and several densitometer heads for sensing printed ink density.

In a different view of the press cylinder 18, shown in FIG. 2, each end of the axle of the cylinder 18 is seen to be supported in bearings in a sidewall 32 of the printing unit 14, and the cylinder 18 is driven at one end through a gear 34. The cylinder 18 is rotationally connected with an angular position encoder 36, which controls the times at which measurements are made by the densitometer heads 20. A great number of densitometer heads 20 may be employed. Three such densitometer heads are illustrated in FIG. 2, where they are shown supported on a rod 37 near the surface of the paper 16 in such a way that their lateral positions parallel to the principle axis of the cylinder 18 can be adjusted.

In the preferred embodiment of the invention being described, printing plates for printing images 38 on the paper 16 include portions for printing in a margin a group of test patches 40 at particular lateral positions where densitometer heads 20 are to be placed. Each of the groups 40 of test patches preferably contains at least one test patch printed by each of the color printing units 12, 14 of the press. Each densitometer head 20 contains six "channels" of sensing equipment for sensing the density simultaneously of six different test patches, and hence can accommodate the output of a six-color printing press. Each of the six channels of each densitometer head 20 has two light sensing apparatuses, one apparatus ordinarily being used for measuring light reflected from a printed test patch and the other being used for measuring light reeflected from an unprinted reference area adjacent the respective printed test patch. Each densitometer head 20 also has one photosensitive detector employed only as an aid in adjusting the time of measurement. Thus each six-channel densitometer head 20 has thirteen photosensitive detectors.

Figure 3:
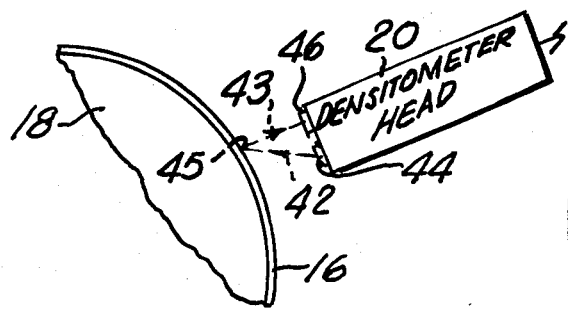
FIG. 3 is a side view of a densitometer head and of a portion of a printing press cylinder with printed paper to be optically measured.

In FIG. 3 a slab-shaped beam of light 42, which is produced by a long flash tube inside the densitometer head 20, emerges from the densitometer head and illuminates a test region 45 of the paper 16 at 45° angle. The light beam 42 emerges from a narrow beam-defining slit 44, which is long enough laterally to illuminate at least one entire group 40 of test patches. After reflection from the paper 16, portions of the light that travel in a direction denoted by an arrow 43, are measured by the densitometer head 20. Light propagating generally in the direction 44 enters 13 circular ports 46, which are arranged in a single line so that each receives light reflected principally from either a particular test patch or an adjacent respective unprinted reference area within the group 40 of test patches.

Figure 4:
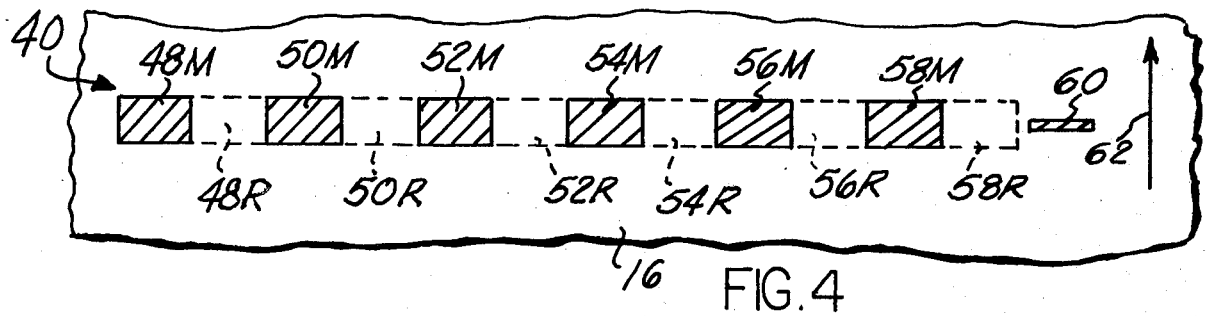
FIG. 4 is a pattern of test patches printed on paper for measurement by the optical densitometer.

The arrangement of a group 40 of test patches is shown in FIG. 4. Each of the cross-hatched rectangular areas 48M, 50M, 52M, 54M, 56M, 58M can be printed by a different printing unit in a six-color printing press, but in the two-unit press employed herein as an example only two of those patches would be printed. If preferred, several patches of a group 40 may be printed in one color by the printing unit 12 and the other patches printed in a second color by the other printing unit 14.

Adjacent to each of the printed test patches 48M ... 58M is an unprinted reference area 48R, 50R, 52R, 54R, 56R, 58R respectively. The printed measurement area 48M and the adjacent unprinted reference area 48R form a pair of areas; measurement data of light reflected from the unprinted reference area 48R is dividied by measurement data of light reflected from its companion printed area 48M in order to correct for variable but common mode factors such as the intensity of the flash of light 42 that illuminates the test areas. Similarly the printed measurement areas 50M and the unprinted reference area 50R adjacent thereto form a pair for data processing purposes, as do the other pairs of measurement and reference areas.

A thirteenth area 60 is printed with a rectangle or stripe whose dimension is small in a direction 62 of movement of the paper 16 with respect to the densitometer head 20. The printed stripe 60 is provided for convenience in adjusting the time at which the light flash occurs for making density measurements. The stripe 60 is illuminated by the same flash of light that illuminates all of the other areas of the group 40, and light reflected from the stripe 60 is received on sensor apparatus within the densitometer head 20.

Accurate measurements depend upon measuring only the relative reflection properties of the measurement area 48M and the unprinted reference area 48R, without distortion from extraneous factors such as the measurement sensitivities of the two sensing apparatuses that measure the reflected light from the two areas. Thus, when the overall measurement sensitivity of the sensing apparatus that measures the measurement area 48M is different from the overall measurement sensitivity of the sensing apparatus that measures the unprinted reference surface 48R, inaccurate results would be produced at the output of the system as a whole if the difference were not compensated.

In the present invention it is not necessary to be certain that the overall sensitivities of the two sensing apparatuses are equal. Instead a preliminary measurement is made that ascertains the relative sensitivities of the two sensing apparatuses, preferably while the press is not printing, and the relative sensitivity data are stored in a memory means. Later, when the press is printing, the reflectivity of pairs of areas such as 48M, 48R are measured, and the data thus obtained are compensated in accordance with the relative sensitivity data read out from the memory means. Correct indications of optical density of the printed ink are therefore provided at the final output of the measurement system.

The relative overall measurement sensitivities of sensing apparatuses for measuring the printed area 48M and its associated unprinted reference area 48R are measured by passing unprinted paper to the densitometer region 45 of the press and operating the densitometer apparatus in a "calibrate" mode. In the calibrate mode the light source is flashed as described above to illuminate the test region 45, but at a time when the entire region 45 has unprinted paper. The sub-areas of the region 45 at which the printed test patch 48M and the unprinted reference area 48R of paper will later be located are denoted as areas 48N and 48P respectively, on the blank paper. Amounts of light reflected from unprinted paper at both of these areas 48N, 48P, are measured Their reflection properties are identical within the limits of accuracy required for the present system. A ratio of their readings is automatically computed to provide a sensitivity ratio for the two respective sensing apparatuses of the densitometer. The logarithm of this sensitivity ratio is automatically computed and stored in memory for use in compensating the measurements that are subsequently to be made while running. Similar calibrations and measurements are made for each other pair 50M, 50R, etc. of press that correspond to the other five measurement channels of the densitometer head 20 being discussed, and for others of the densitometer heads 20.

Conventional multiplexing apparatus is employed in the electronic measurement circuits of the densitometer in order that some of the subcircuits may be employed in common by more than one of the sensing apparatuses and channels. It is not necessary to describe the multiplexers to illustrate the invention; for clarity they are omitted and only the measurement channel corresponding to the pair of areas 48M, 48R is described. The calibration of the densitometer apparatus is described first hereinbelow, after which the running operation is described.

Figure 5:
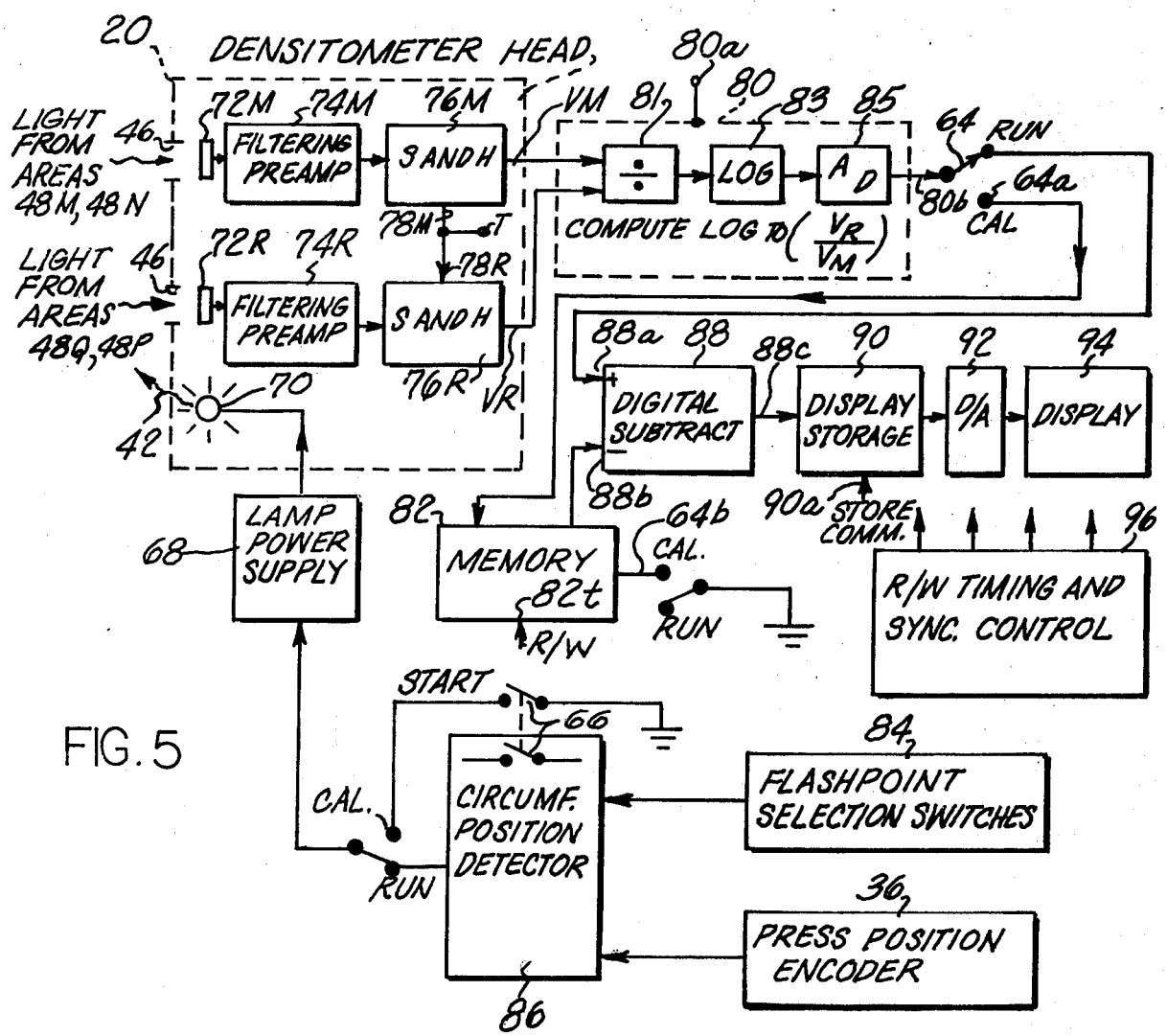
FIG. 5 is a block diagram of electronic circuits of the densitometer.

Referring now to FIG. 5 a "Run, Calibrate" switch 64 is first placed in a Calibrate position 64a by the operator. Unprinted paper is run into the press to a position at the test region 45. A Start switch 66 is then depressed by the operator to start a calibration routine. In response thereto a lamp power supply 68 receives a flash command and the power supply 68 energizes a flash lamp 70 to produce the long thin beam of light 42 to illuminate the paper at the test region 45. Because no part of the paper 16 is printed, the areal portions at the locations 48N and 48P of the test region 45 have identical reflectivity. Light is reflected from these locations into respective ports 46 of the densitometer head 20, where it is conducted by optical apparatus (not shown) to respective photosensitive detection means 72M, 72R, which are preferably photodiode transducers.

Electrical signals whose values depend upon the intensities of the light from the locations 48N, 48P are produced by the photodiodes 72M, 72R respectively and conducted to filtering preamplifiers 74M, 74R. The preamplifiers 74M, 74R filter their respective signals to reduce noise, and amplify them somewhat, applying the resulting signals to respective sample and hold devices 76M, 76R. The sample and hold devices are actuated simultaneously at command terminals 78M, 78R respectively by a synchronized timing signal, to store simultaneous measurements of light reflected from the areas 48N, 48P, of the unprinted paper.

An electrical output signal $V_M'$ from the "measurement" sample and hold device 76M and a signal $V_R'$ from the "reference" sample and hold device 76R are both conducted a computation circuit 80. One embodiment of the computation circuit 80 is described in very great detail in the above referenced patent.

Preferably, the computation circuit 80 comprises an analog divider 81, which receives the two voltage signals $V_M'$ and $V_R'$, and divides $V_R'$ by $V_M'$ to produce an output quotient. Analog dividers of this type are commercially available from many manufacturers, including Burr-Brown Research Corporation of International Airport Industrial Park, Tuscon, Ariz., which offers one as Model 4290. The effects of lamp intensity on the readings cancel out of the ratio $V_R'/V_M'$, because $V_R'$ and $V_M'$ are measured with the same flash of light 42.

The value of the voltage $V_M'$ is presumed to be a product of two factors, namely the reflectivity of the area 48N and the sensitivity of the respective sensing apparatus. The voltage $V_R'$ is similarly assumed to be a product of a reflectivity and a sensitivity. The effects of relative reflectivities of the two surfaces cancel out of the ratio $V_R'/V_M'$ because $V_R'$ and $V_M'$ are measurements of similar unprinted surfaces 48N, 48P that have substantially equal reflectivity. Consequently the ratio $V_R'/V_M'$ represents only the relative measurement sensitivities of the two sensing apparatuses.

The output of the analog divider 81 is connected to an analog logarithmic amplifier 83, whose function is to produce a signal at its output proportional to the logarithm of a signal at its input. Devices of this type are also very commonly available commercially, Burr-Brown offering one as Model 4116. An output signal of the analog logarithmic amplifier 83 is applied to a conventional analog-to-digital converter 85, whose digital output signal at a terminal 80b is in a binary form, which is convenient for storage in a memory device.

Output data at the terminal 80b of the computation circuit 80 are conducted through the terminal 64a of the "Run, Calibrate" switch 64 to a memory means 82, where they are stored. The memory device 82 is in a "write only" mode of operation during calibration, being maintained in that mode by a ground potential signal at a control terminal 64b of the switch 64. Thus data representing log 10 $(V_R'/V_M')$ for entirely unprinted paper are stored in the memory 82, which step completes the calibration procedure.

To operate the apparatus in a run mode the "Run, Calibrate" switch 64 is placed in a "Run" position, FIG. 5, and the press 10 is operated to print images 38 in ink on the paper 16. The densitometer start switch 66 is again depressed. When the angular position of the press position encoder 36 reaches a code corresponding to the settings of a set of flash point selection switches 84, a circumferential position detector 86, which is a digital coincidence comparator, produces an output signal that serves as a flash command. The lamp power supply 68 is triggered by the flash command and the lamp 70 is energized. At that instant a group 40 of test patches is at the test region 45 under the densitometer head 20. Light 42 from the flash lamp 70 is reflected from the measurement test patch area 48M and from the adjacent reference area 48R, and reflected light therefrom falls upon the photodiodes 72M, 72R, respectively as before. Shortly thereafter the sample-and-hold modules 76M, 76R are actuated to hold the signals that they are then receiving, so that they produce and hold output signals $V_M, V_R$, corresponding to the amounts of light reflected from the areas 48M, 48R respectively. A computation is then made in the computation circuit 80, upon a command at the timing terminal 80a. The log $_{10}$ $(V_R/V_M)$ is computed and appears, after analog to digital conversion, at the terminal 80b. The effects of lamp intensity cancel out of the ratio $V_R/V_M$ because $V_R$ and $V_M$ are measured with one flash of light in common.

This logarithm signal is conducted to one input terminal 88a of a digital subtraction circuit 88. At the same time the contents $\log_{10}(V_R'/V_M')$ of the memory 82 are read and applied to a subtrahend input terminal 88b of the digital subtractor 88. The data at the terminal 88b are subtracted linearly from the data at the terminal 88a to produce at an output terminal 88c a signal representing the quantity $\log_{10}(V_R/V_M) - \log_{10}(V_R'/V_M')$, which is equal to $\log_{10}[(V_R/V_M)(V_M'/V_R')]$.

In the final resulting output data at terminal 88c, effects of the relative sensitivities of the two sensing apparatuses cancel out because the ratio $(V_M'/V_R')$ cancels the relative sensitivity effects that are inherent in the ratio $(V_R/V_M)$. Consequently the final output data represents only the relative reflectivities of the printed patch 48M and the unprinted adjacent reference area 48R, which is the only information of interest. The output data have therefore been compensated for differences in measurement sensitivities, for example gain differences between the sensing apparatuses having the subscripts An output signal from the digital subtractor 88 is stored in a display storage memory device 90 upon a store command at a terminal 90a, and thereafter is displayed on an operator's display device 94, which conveniently may include a cathode ray tube. A digital-to-analog converter 92 converts the digital data of the display storage memory 90 to an analog signal to drive the cathode ray tube display device 94.

A read-write timing and synchronization control device 96 provides timing and synchronization signals according to routine design techniques to various circuits of the densitometer apparatus, for example, to the timing terminals 78M, 78R, the read-write terminal 82t of the memory 82, etc. All of the circuit modules of FIG. 5 are conventional ones that are well known to those skilled in the electronic arts.

A method for making optical density measurements of ink printed by a printing press has been described in which it is not necessary to adjust the relative sensitivities of measurement and reference sensing apparatus in order to make accurate measurements of the reflection density of ink printed by the printing press. Ink density measurements made during operation of the press are automatically corrected to compensate for differences in sensitivities by employing calibration data that were previously measured with unprinted paper in the press. The calibration data are stored in a memory and used repeatedly thereafter to compensate subsequently obtained data.

What is claimed is:

1. The method of compensating densitometer readings where the densitometer is used to measure the relative optical density of a printed area during a printing operation on material in which densitometer light is directed onto the printed area of said material and transmitted therefrom along a first optical path with a characteristic of the transmitted light varying in accordance with the optical density, and densitometer light is directed onto an unprinted area of said material and transmitted therefrom along a second optical path to provide a reference light value, with the light along said paths being sensed by different optical sensing means to provide separate electrical test signals from which the relative optical density of the printed area is derived comprising the steps of substituting first and second calibration areas for the printed and unprinted areas when the press is not printing, second calibration area having the same light transmittting characteristics as said first calibration area, utilizing first and second optical sensing means for respectively sensing the light transmitted along said first and second paths to respectively provide first and second calibration signals in order to determine differences between said calibration signals, and deriving calibration data from said calibration signals, storing said calibration data in a memory means, measuring the apparent relative optical density of a printed area when the press is printed by transmitting light along said paths to a printed area and an unprinted area and utilizing said first and second sensing means for respectively sensing the light of said first and second paths to provide said separate electrical test signals, and deriving measurement data therefrom, reading said calibration data from said memory means, and combining said measurement data and said calibration data to produce an indication of the actual relative optical density of said printed and unprinted areas.

2. The method of compensating densitometer readings as defined in claim 1 and wherein said step of sensing the light to provide calibration signals comprises sensing first and second amounts of light, from a common source, reflected from each of said first and second calibration areas respectively, and wherein said step of deriving calibration data from said calibration signals comprises computing a first logarithm of a ratio of said first and second amounts of light, and wherein said step of measuring the apparent relative optical density of said printed and unprinted areas comprises sensing the amount of light from a common source reflected from each of said printed and unprinted areas, and wherein said step of deriving measurement data therefrom comprises computing a second logarithm of a ratio of the latter two amounts of light, and wherein said step of combining comprises combining said first logarithm corresponding to said callibration data and said second logarithm corresponding to said measurement data by linear algebraic addition.

3. The method of compensating densitometer readings as defined in claim 1 and wherein said step of substituting first and second calibration areas comprises putting unprinted material in the press.

4. The method of compensating densitometer readings as defined in claim 1 and wherein both of said steps of sensing the light of said first and second paths comprise sensing said light of said first and second paths by means of said first and second respective sensing means having respective light sensors of different overall measuring sensitivities.

* * * * *